US012797089B2

(12) United States Patent
Batchelor et al.

(10) Patent No.: US 12,797,089 B2
(45) Date of Patent: Nov. 17, 2026

(54) FORCE CONTROL SYSTEMS AND METHODS FOR LITHOTRIPSY

(71) Applicant: GYRUS ACMI, INC., Westborough, MA (US)

(72) Inventors: Kester Julian Batchelor, Mound, MN (US); David M. Leak, Brooklyn Park, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 108 days.

(21) Appl. No.: 19/021,478

(22) Filed: Jan. 15, 2025

(65) Prior Publication Data

US 2025/0235223 A1 Jul. 24, 2025

Related U.S. Application Data

(60) Provisional application No. 63/624,129, filed on Jan. 23, 2024.

(51) Int. Cl.

*A61B 17/22* (2006.01)
*A61B 90/00* (2016.01)
*A61B 17/00* (2006.01)

(52) U.S. Cl.

CPC ........ *A61B 17/22012* (2013.01); *A61B 90/08* (2016.02); *A61B 2017/00022* (2013.01); *A61B 2017/00115* (2013.01); *A61B 2017/22025* (2013.01); *A61B 90/06* (2016.02); *A61B 2090/064* (2016.02); *A61B 2090/0807* (2016.02); *A61B 2217/005* (2013.01)

(58) Field of Classification Search

CPC ...... A61B 2090/064; A61B 2090/0807; A61B 90/06; A61B 90/08; A61B 17/22; A61B 17/22012; A61B 17/2202; A61B 2017/00022; A61B 2017/00115; A61B 2017/22017; A61B 2017/22025; A61B 2017/22079; A61B 2017/005

See application file for complete search history.

(56) References Cited

U.S. PATENT DOCUMENTS 7,303,106 B2 * 12/2007 Milliman ............ A61B 17/068 227/181.1
9,421,023 B2 8/2016 Bond et al.
11,452,574 B1 * 9/2022 Dunki-Jacobs .............................. A61B 17/07207
11,684,148 B2 6/2023 Farrell et al.

(Continued)

*Primary Examiner* — Phong Son H Dang
(74) *Attorney, Agent, or Firm* — Schwegman Lundberg & Woessner, P.A.

(57) ABSTRACT

A lithotripsy device comprises a feedback device for providing force indicia generated during a lithotripsy procedure. The feedback device comprises a slide configured to attach to a handpiece of a lithotripsy device, a positioning device connected to the slide to adjust a position of the slide relative to the handpiece, and a feedback indicator connected to the slide to provide feedback related to a force being applied to the slide to displace the slide relative to the handpiece. A method of performing a lithotripsy procedure comprises contacting a stone with a shaft extending from a handle of a lithotripsy device, applying energy from the shaft to the stone to fragment the stone, applying a force to the stone from the shaft via the handle to facilitate transfer of the energy to the stone, and providing an output of an amount of force that the shaft contacts the stone.

15 Claims, 12 Drawing Sheets

(56) References Cited

U.S. PATENT DOCUMENTS

| | | | | |
|---|---|---|---|---|
| 2016/0106450 | A1 | 4/2016 | Hanna et al. | |
| 2022/0304720 | A1 * | 9/2022 | Jamous ............ | A61B 17/32053 |
| 2022/0395348 | A1 * | 12/2022 | Nicholas ............ | A61B 17/1155 |

* cited by examiner

FORCE CONTROL SYSTEMS AND METHODS FOR LITHOTRIPSY

PRIORITY CLAIM

This application claims the benefit of priority to U.S. Provisional Patent Application Ser. No. 63/624,129, filed on Jan. 23, 2024, the contents of which are incorporated herein by reference.

TECHNICAL FIELD

The present disclosure relates generally, but not by way of limitation, to medical devices that can be used to break obstructions, such as physiological calculi or "stones" using lithotripsy.

More specifically, the present disclosure relates, but not by way of limitation, to systems, devices and methods for lithotripsy systems for applying break-up force to stone fragments.

BACKGROUND

Medical endoscopes were first developed in the early 1800s and have been used to inspect inside the body. A typical endoscope includes a distal end comprising an optical or electronic imaging system and a proximal end with controls for manipulating tools and devices for viewing the image, with a solid or tubular elongate shaft connecting the ends. Some endoscopes allow a physician to pass tools or treatments down one or more hollow working channels, for example, to resect tissue or retrieve objects.

Over the past several decades, several advances have been made in the field of endoscopy, and in particular relating to the breaking up of physiologic calculi in the bile ducts, urinary tract, kidneys, and gall bladder. Physiological calculi in these regions may block ducts and cause a patient to experience a substantial amount of pain. Therefore, these calculi are typically broken down for surgical removal or biological passing. Different techniques and procedures have been developed to break up stones, including ultrasonic lithotripsy, pneumatic lithotripsy, electro-hydraulic lithotripsy (EHL), and laser lithotripsy including dissolution of calculi using green light, YAG, or holmium lasers.

SUMMARY

The present inventors have recognized, among other things, that problems to be solved in performing lithotripsy procedures is the difficulty in applying force from a lithotripsy device to a stone. For example, lithotripsy devices can involve the use of a shaft to deliver acoustic energy to break-up the stones. Acoustic energy can include sound waves, sonic waves, ultrasonic waves or shock waves, or any combination of these. In order to transmit the acoustic energy to the stones, it is desirable to contact the tip of the lithotripsy shaft to the stone. As such, there is skill involved in applying the acoustic energy to the stone. In particular, the present inventors have recognized that the breaking apart of the stones is most efficiently achieved while applying the tip of the lithotripsy shaft to the stones within a particular range of forces. For example, not applying sufficient force to the stone can result in not enough acoustic energy being transferred to the stone, thereby resulting in the breakdown process taking longer. Additionally, if too much force is applied to the stone, the tip of the lithotripsy shaft can get bogged down and the acoustic energy might not properly form, thereby also slowing down the breakdown process.

The present subject matter can provide solutions to this problem and other problems by providing a lithotripsy device that includes an indication of the amount of force being applied by the lithotripsy device to the stone. In particular, the present subject matter can provide an indication of the amount of force a user is applying to a lithotripsy shaft in real time such that the user can make intraoperative adjustments. In examples, force control devices of the present disclosure can provide analogue or digital output, such as visual, audio or tactile feedback, of how much force a user is applying to a handle of a lithotripsy shaft, which replicates the amount of force a lithotripsy shaft applies to a stone. In examples, force control devices of the present disclosure can comprise add-on components that can be attached to a handle of a lithotripsy device, but can additionally comprise integrated devices. In examples, force control devices of the present disclosure can be combined with other add-on features, such as filters and suction control valves.

In an example, a lithotripsy device can comprise a feedback device for providing force indicia generated during a lithotripsy procedure. The feedback device can comprise a slide configured to attach to a handpiece of a lithotripsy device, a positioning device connected to the slide to adjust a position of the slide relative to the handpiece, and a feedback indicator connected to the slide to provide feedback related to a force being applied to the slide to displace the slide relative to the handpiece.

In another example, a method of performing a lithotripsy procedure can comprise contacting a stone with a shaft extending from a handle of a lithotripsy device, applying energy from the shaft to the stone to fragment the stone, applying a force to the stone from the shaft via the handle to facilitate transfer of the energy to the stone, and providing an output of an amount of force that the shaft contacts the stone.

This overview is intended to provide an overview of subject matter of the present patent application. It is not intended to provide an exclusive or exhaustive explanation of the invention. The detailed description is included to provide further information about the present patent application.

Figure 1:
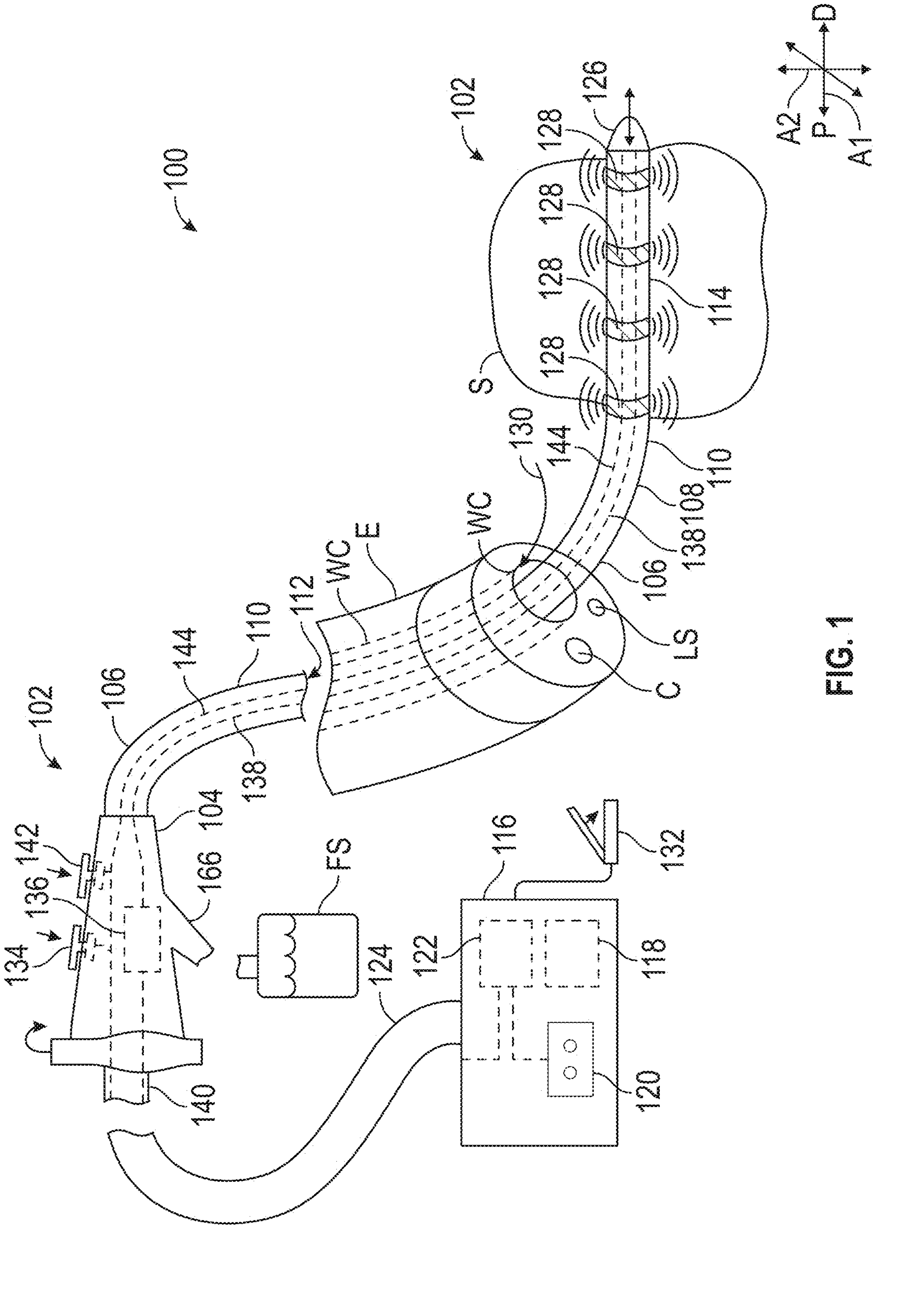
FIG. 1 is a schematic view of an illustration of an exemplary lithotripsy system with which the various stone fragment capture devices and systems of the present disclosure can be used.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure provides examples of devices, systems and methods that can help address problems associated with fragmenting stones during lithotripsy procedures. In particular, the present disclosure provides examples of devices, systems and methods that can be used to monitor and control engagement of a lithotripsy device with a biological target, such as a physiological calculi or “stone.” For example, the devices, systems and methods of the present disclosure can provide an output, e.g., visual, audio or tactile feedback, that provides an indication of the amount of force that a lithotripsy device is applying to a stone. The output can additionally provide an indication if too little force, an appropriate amount of force or too much force is being applied. Benefits of the approaches described herein include, among other things, improving the ability of the lithotripsy device to break-up or fracture stones, breaking up of stones into smaller pieces, which can facilitate extraction of the stone fragments, and lowering the time it takes to break-up a stone, which can facilitate shorter procedure times.

FIG. 1 illustrates an isometric view of an example of lithotripsy system 100 including lithotripter 102 having housing 104, such as a handle. Lithotripter 102 can include delivery member 106 that is deliverable to a treatment site through working channel WC of endoscope E. Endoscope E can also include light source LS and camera C.

Delivery member 106 can include elongate shaft 108 having a tubular structure that can be flexible or rigid. Suitable materials for the delivery member include, but are not limited to, polytetrafluoroethylene (“PTFE”), polyethylenes (“PE”) and polyamides. Elongate shaft 108 can include outer surface 110 and at least one lumen 112 extending therethrough, the lumen being suitable for passage of components and materials that communicate with end effectors described herein.

Delivery member 106 can include an end effector such as probe 114 at a distal end that is deliverable to a treatment site. Probe 114 can be configured to deliver energy to fragment a mobile calculus such as a stone located in a bile duct, urinary tract, kidney or gall bladder. Probe 114 of lithotripter 102 can be introduced into a patient, driven by delivery member 106 through working channel WC of endoscope E or similar instrument. Probe 114 can be flexible or rigid.

Lithotripter 102 can be connected to signal generator 116. Signal generator 116 can include power source 118 or can be couplable to an external power source. Signal generator 116 can also include input 120 to receive an instruction from an operator, and can include controller 122 having processing circuitry for determining actions based on operator input and for sending control signals via output 124 for communication to lithotripter 102. Signal generator 116 can comprise an energization source that can produce signals and send the signals to probe 114 of lithotripter 102 to cause probe 114 to emit acoustic energy. Acoustic energy can include sound waves, sonic waves, ultrasonic waves or shock waves, or any combination of these. Acoustic energy can be delivered to stone S to deteriorate, crack and thereby fracture stone S. The examples herein are described with reference to combinations of ultrasonic and shock wave applications but any suitable acoustic energy, or combinations thereof, for fracturing stones can be provided. The terms sonic and ultrasonic may be used herein interchangeably, and can include any suitable acoustic energy for fragmenting stones. In additional examples, lithotripter 102 can be configured to deliver pneumatic, hydraulic or laser energy.

Features of probe 114 can provide improved fragmenting of stone S. For example, probe 114 can include drill 126 (which need not include a rotating drill bit), such as an ultrasonic drill that emits acoustic energy, in longitudinal direction A1, to drill a hole in the stone. In example, longitudinal direction A1 can extend in the proximal-distal, P-D, direction. Probe 114 can also include one or more lateral ultrasonic emitters 128 such as a lateral ultrasonic transducer to deliver acoustic energy inside the hole to fragment the stone from the inside out, such as by applying acoustic energy in radial or lateral direction A2. Lateral ultrasonic emitters 129 can emit ultrasonic energy radially relative to the axis of delivery member 106.

Drill 126 can be coupled to elongate shaft 108 and can be located at a distal tip of probe 114. Drill 126 can include at least a portion that extends distal of elongate shaft 108. In the example of FIG. 1, drill 126 can be configured to emit ultrasonic energy in longitudinal direction A1. Drill 126 can cause mechanical modification or destruction of stone S by producing pulsatile shock waves that move generally along longitudinal direction A1. Drill 126 can be configured to drill a hole, such as a recess into, or passage through, stone S. FIG. 1 shows an example including drill 126 that has drilled passage through stone S.

Drill 126 can be an ultrasonic emitter that receives ultrasonic energy from a remotely located ultrasonic drill transducer, which will be referred to as drill transducer 136 for the purposes of clarity over other emitters and transducers in this disclosure. Drill transducer 136 can be located, for example, in housing 104 of lithotripter 102. Drill transducer 136 can transmit ultrasonic energy in generally longitudinal direction A1, distally out of housing 104. Ultrasonic energy can be transmitted from drill transducer 136 to drill 126 via ultrasound transmission member 138. Ultrasound transmission member 138 can be coupled to drill transducer 136 at a proximal end and to drill 126 at the distal end. Ultrasound transmission member 138 can be formed of any material that is capable of transmitting the ultrasound energy from drill transducer 136 to drill 126, including but not limited to metal, metal alloys, shape memory alloys, polymers, ceramics, fibers, crystals or composites thereof.

Drill transducer 136 can be electrically couplable to signal generator 116, such as by connector 140, to receive signals for operating drill 126. Drill transducer 136 can be actuated by, for example, an operator depressing foot pedal 132 that is in electrical communication with signal generator 116, or can be actuated by drill actuator 134 coupled to housing 104 that is in electrical communication with signal generator 116. Additionally, or alternatively, the drill transducer 136 may be operated based on the input 120 from the operator and/or the actions determined by the controller 122. Any other suitable actuator for controlling activation of drill 126 can be provided.

In addition to using an ultrasonic emitter for drilling, probe 114 can include at least one lateral ultrasonic emitter 128 configured to direct ultrasonic energy in radial or lateral direction A2, outward and away from longitudinal direction A1 such as toward an internal surface (e.g., an internal passage) of stone S. In the example of FIG. 1, the at least one lateral ultrasonic emitter 128 includes a plurality or array of lateral ultrasonic emitters 128.

Each of lateral ultrasonic emitters 128 can direct ultrasonic energy in lateral direction A2, with each of lateral ultrasonic emitters 128 located along a different longitudinal position on probe 114. In some examples lateral ultrasonic emitters 128 can be spaced apart along longitudinal direction A1. Lateral ultrasonic emitters 128 can extend laterally or radially around probe 114. In some examples, lateral ultrasonic emitters 128 can extend around the entire three-hundred-sixty-degree circumference of probe 114, or around a perimeter of probe 114 when a probe has a non-circular cross-section in direction lateral or perpendicular A1 to longitudinal direction A1. In other examples, lateral ultrasonic emitters 128 can only partially wrap around probe 114.

Lateral ultrasonic emitters 128 can be located proximal of drill 126. A benefit of this arrangement is that lateral ultrasonic emitter 128 can follow drill 126 so that after drill 126 prepares the internal passage in stone S, lateral ultrasonic emitter 128 can be advanced through the internal passage. When activated, such as by lateral emitter actuator 142 that is in electrical communication with lateral ultrasonic emitters 128 via electrical element 144 such as a wire, lateral ultrasonic emitters 128 can be configured to emit ultrasonic energy into to the internal passage and internal to stone S to fracture stone S from the inside of stone S.

Similar to drill transducer 136, lateral ultrasonic emitter 128 can include an ultrasonic or other acoustic transducer. An electrical-to-acoustic transducer is a component that can convert an electrical signal into variations in a physical quantity such as sound waves or pressure. Ultrasonic transducers can include linear piezoelectric stacks having piezoelectric elements located between two metal plates. In additional examples, magneto-restrictive stacks can be used. Such piezoelectric elements can convert electrical energy (e.g., electric current) into mechanical energy (e.g., sound waves, sonic waves, ultrasonic waves, shock waves). Piezoelectric elements can include crystal, such as quartz, having physical characteristics that results in the crystal undergoing mechanical stress when subjected to an electric field that causes the crystal to change size or shape. The piezoelectric elements or alternatively expand and contract in response to an alternating electric field, such as can be supplied by signal generator 116. This expansion and contraction can generate sound waves that can be delivered to stone S to fracture stone S.

To help locate stone S relatively stationary relative to working channel WC of endoscope E while drilling the hole, and relatively stationary to probe 114 (except for longitudinal A1 movement of probe 114 through the stone), suction 130, as denoted by an arrow, can be applied through working channel WC. Suction 130 can cause stone S to be "captured" by pulling stone S towards working channel WC and thus pulling stone S towards drill 126 of probe 114 for drilling. Upon fracturing of stone S, stone fragments can be suctioned into working channel WC.

Some lithotripsy systems described herein can include fluid input 166 for receiving fluid from fluid storage FS and delivering fluid to a treatment site. For example, irrigation fluid or lavage fluid can be transmitted through endoscope E or elongate shaft 108. Typical stone fragment recovery systems involve simply collecting a mixture of solids and liquids retrieved from the patient while performing the procedure. For example, suction 130 can be applied at distal end of endoscope E or elongate shaft 108, and a vacuum drawn therethrough to deposit, materials, e.g., stone fragments and waste fluid, into a waste container. In examples, tube 150 can be connected to housing 104 to fluidly couple a lumen extending through working channel WC of endoscope E with collection container 152. Tube 150 can additionally be connected to suction device 154 or a pump to draw a vacuum through working channel WC, indicated by the arrow of suction 130, as explained in greater detail with reference to FIG. 3.

As discussed herein, the ability of probe 114 to apply acoustic energy to stone S can depend on the amount of force with which delivery member 106 applies drill 126 and lateral ultrasonic emitters 128 to stone S. For example, desirable transmission of ultrasonic energy from drill 126 can depend on the amount of force that probe 114 applies to stone S in longitudinal direction A1, and desirable transmission of ultrasonic energy from lateral ultrasonic emitters 128 can depend on the amount of force that probe 114 applies to stone S in radial or lateral direction A2. With the present disclosure, lithotripsy system 100 can be equipped with a feedback system to provide indicia of the amount of magnitude being applied by probe 114 to stone, as well as feedback or guidance as to how to appropriately adjust the force to achieve a desired outcome.

Figure 2:
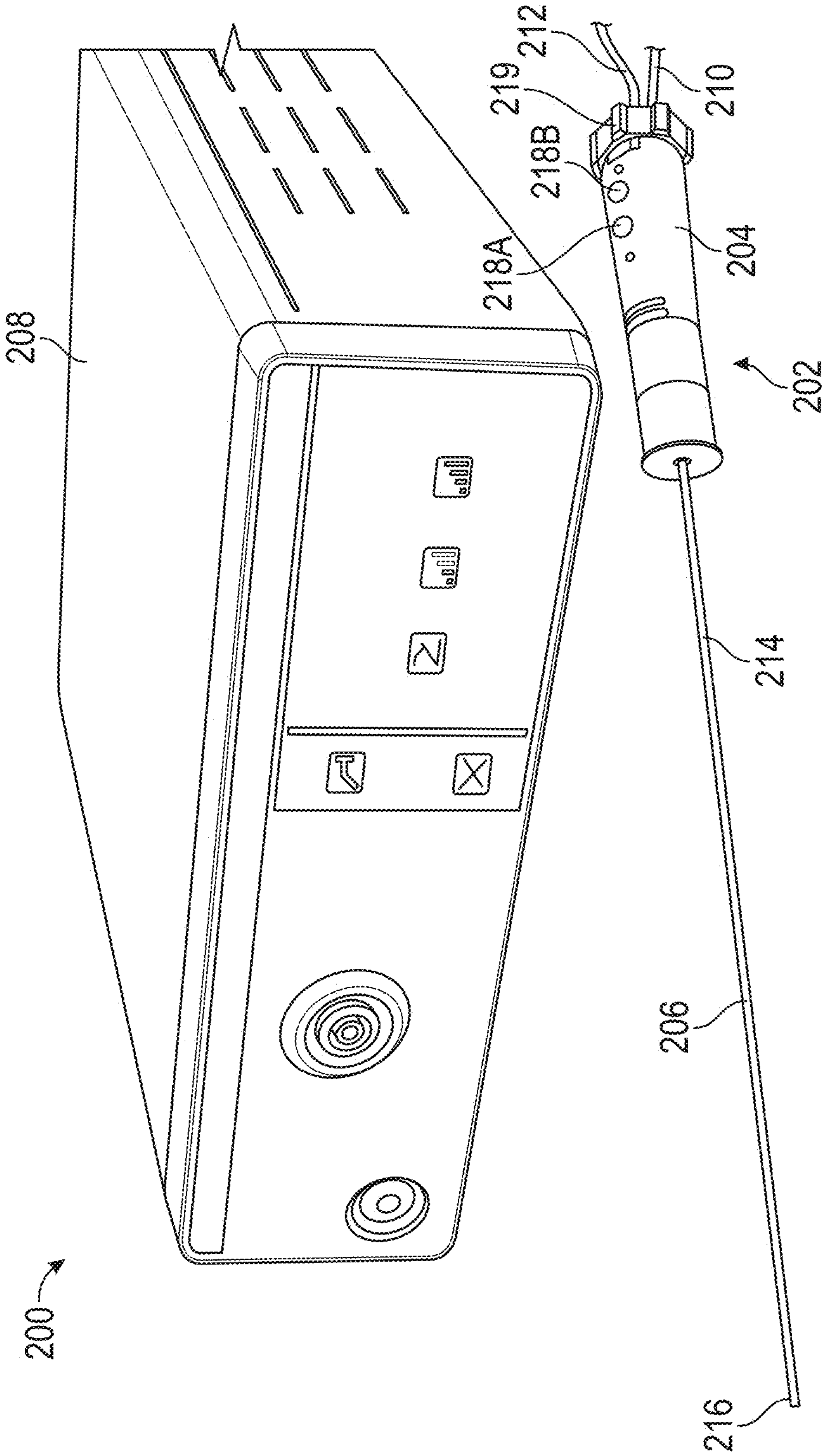
FIG. 2 is a perspective view of a lithotripsy system comprising a hand-held probe configured to deliver high frequency and ultrasonic energy for the fragmentation of stones.

FIG. 2 is a perspective view of lithotripsy system 200 comprising hand-held probe 202 configured to deliver high frequency and ultrasonic energy for the fragmentation of stones. In examples, lithotripsy system 200 can comprise an oscillating lithotripter as is described in U.S. Pat. No. 9,974,552 to St. George et al. titled "Oscillating Lithotripter" and which is assigned to Gyrus ACMI, Inc., the contents of which is incorporated herein in its entirety. Features of the present disclosure can be added into lithotripsy system 200. Furthermore, lithotripsy system 200 can comprise an example of lithotripsy system 100 of FIG. 1.

Hand-held probe 202 can comprise handpiece or handle 204 and shaft 206. Hand-held probe 202 can be connected to generator console 208, such as via cable 210. Collection tube 212 can be connected to a storage container, such as fluid storage FS (FIG. 1) or container 232 (FIG. 3), to collect fluid and other biological material collected via shaft 206. Shaft 206 can extend from proximal end 214 to distal end 216 and can comprise an internal lumen. Handle 204 can further comprise button 218A and button 218B to control activation energy and knob 219 to control suction level.

Figure 3:
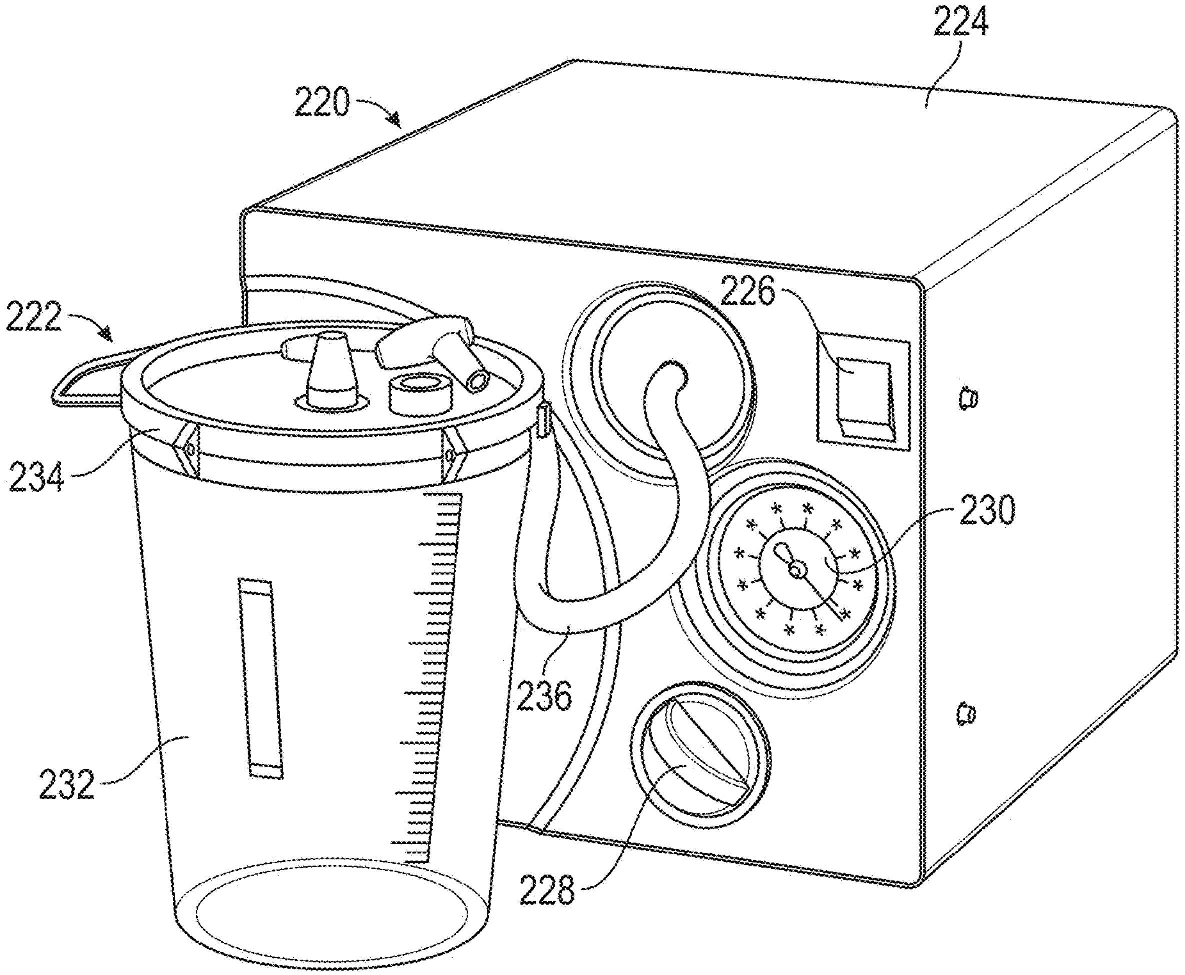
FIG. 3 is a perspective view of a suction pump and a stone capture canister suitable for use with the lithotripsy system of FIG. 2.

FIG. 3 is a perspective view of suction pump 220 and stone fragment canister 222. Suction pump 220 can comprise housing 224, power switch 226, suction knob 228 and indicator 230. Stone fragment canister 222 can comprise container 232 and lid 234. Stone fragment canister 222 can be connected to suction pump 220 via tube 236.

Figure 4:
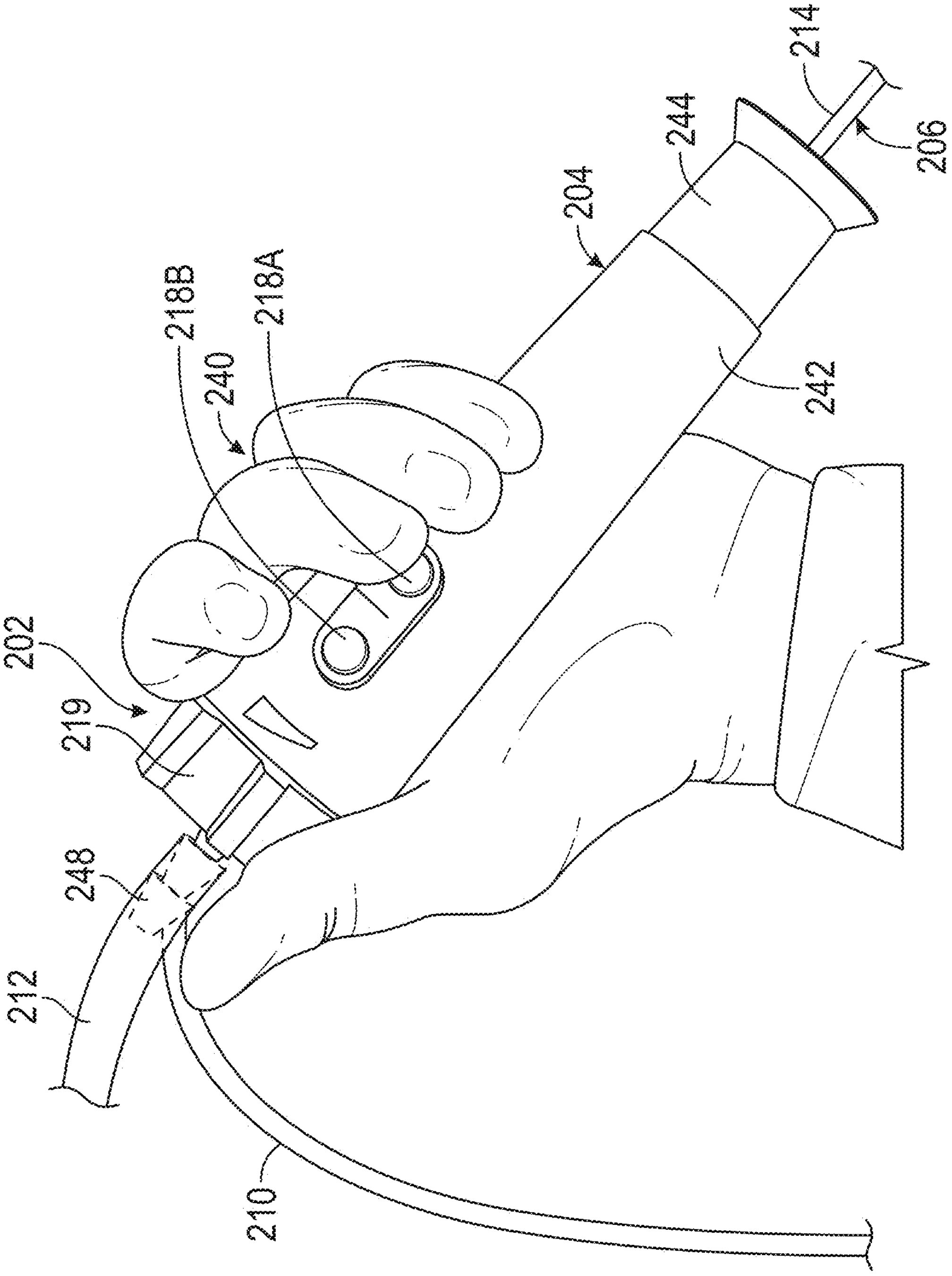
FIG. 4 is a close-up perspective view of a handpiece of the hand-held probe of FIG. 2 in the hand of a user.

FIG. 4 is a perspective view of handle 204 in hand 240 of a user. Handle 204 can comprise handpiece 242. Knob 219 can be positioned at a proximal end of handpiece 242 and nosecone 244 can be positioned at a distal end of handpiece 242. Cable 210 and collection tube 212 can also be connected to a proximal end of handpiece 242.

Figure 5:
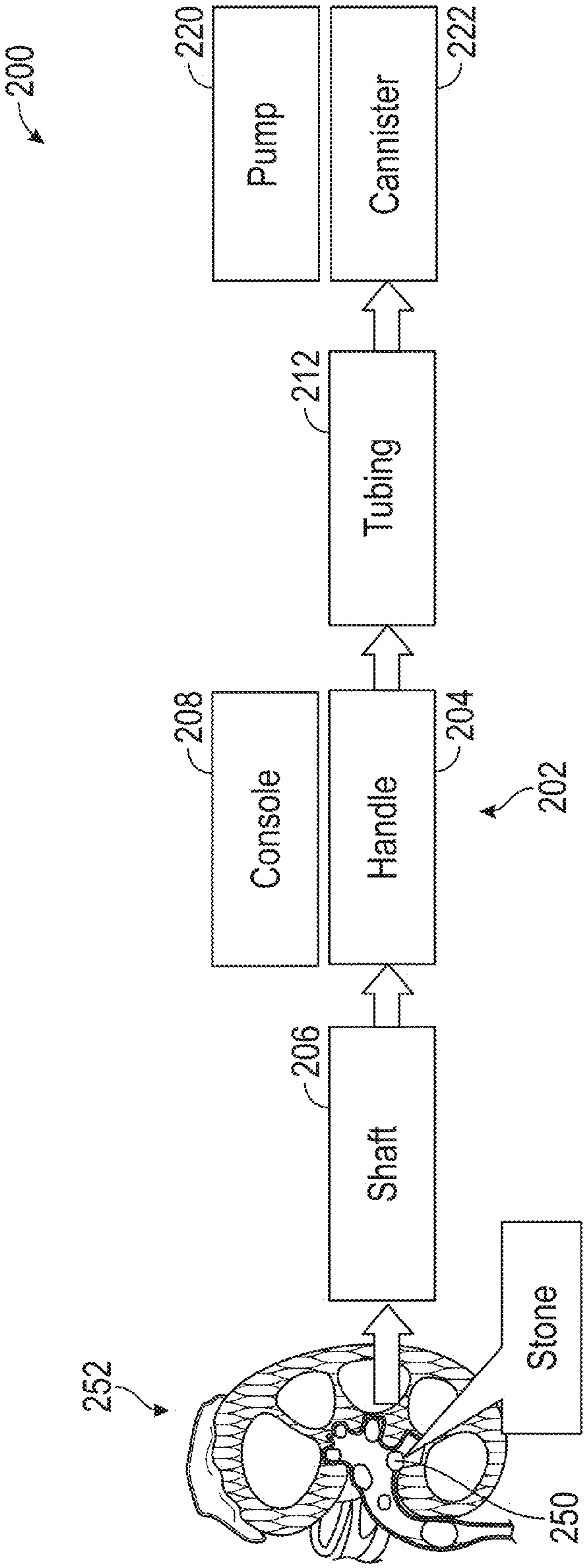
FIG. 5 is a schematic diagram of components of the lithotripsy system and suction system of FIG. 2 through FIG. 4 interacting with a kidney.

FIG. 5 is a schematic diagram of components of lithotripsy system 200 and suction pump 220 of FIG. 2 through FIG. 4 interacting with stone 250 of kidney 252. As discussed with reference to FIG. 3, FIG. 4 and FIG. 5, lithotripsy system 200 can comprise hand-held probe 202, suction pump 220 and stone fragment canister 222. Hand-held probe 202 can comprise shaft 206 and handle 204. Handle 204 can be connected to generator console 208 via cable 210. Handle 204 can be connected to stone fragment canister 222 via collection tube 212, and stone fragment canister 222 can be connected to suction pump 220.

FIG. 2 through FIG. 5 are discussed concurrently.

Lithotripsy system 100 of FIG. 1 and lithotripsy system 200 of FIG. 2 are examples of lithotripsy system that can be used with the force-indicator and filtering devices of the present disclosure, as well as the associated methods described herein. For example, a force indicator device can be connected to housing 104 (FIG. 1) or handle 204 (FIG. 2) to provide a user with an indication of how much force elongate shaft 108 or shaft 206 is applying to a stone or another biological element. Likewise, a force indicator device of the present disclosure can include a filtering member for filtering stone fragments from suction fluid before entering collection tube 212, as well as suction flow control member, as discussed with reference to FIG. 9. Although the present application is described with reference to lithotripsy systems used for retrieval of stones, other types of surgical devices and endoscopy devices can be used with force indicator and filtering devices and methods disclosed herein. For example, any surgical device that can be configured for insertion into a patient that involves application of force along a shaft or body can benefit from the present disclosure. Examples of surgical devices that can be used with the present disclosure can utilize various energy sources, such as laser energy, ultrasound energy, and the like, for cracking, fragmenting, and/or dusting particles, such as stones and other solid or rigid bodies.

With particular reference to FIG. 2, handle 204 can comprise any device suitable for facilitating manipulation and operation of shaft 206. Handle 204 can be located at proximal end 214 of shaft 206 or another suitable location along shaft 206. In examples, handle 204 can comprise a pistol grip, a knob, a handlebar grip and the like. In addition to or alternatively to buttons 218A and 218B and knob 219, handle 204 can comprise one or more of buttons, triggers, levers, knobs, dials and the like for control of energy activation, suction, irrigation and the like.

In various examples, distal end 216 of shaft 206, or another suitable location along shaft 206, can include a surgical device, which can comprise a component or device for interacting with a patient, such as those configured to cut and cauterize tissue and/or produce a desired tissue effect of the patient. In examples, the surgical tool can comprise forceps, a cutting tool, an ablation electrode, a cryogenic needle or applicator, an ultrasonic probe tip and the like, and combinations thereof. As such, hand-held probe 202 can be provided with a linkage, such as a mechanical linkage to actuate forceps or a cutting tool, an electrical linkage to activate an ablation electrode, an acoustic linkage, a liquid conduit (e.g., for the delivery of cryogenic argon gas) and the like, and combinations thereof. In examples, the surgical device can be included on a device used in conjunction with hand-held probe 202. In additional examples, hand-held probe 202 can comprise, or can be combined with, a device for viewing the patient, such as optical devices including endoscopes (e.g., endoscope E of FIG. 1) and fiberscopes.

Generator console 208 can comprise a source of energy for hand-held probe 202. For example, generator console 208 can be configured to provide electricity for performing ablation and cauterizing functions and/or ultrasonic energy for providing cutting, coagulating, fragmenting or other types of surgical functions. In examples, generator console 208 can provide ultrasonic wave energy, while intermittent ballistic shockwave energy is provided via an oscillating free mass within handle 204.

Shaft 206 can comprise an elongate member configured to deliver energy for fragmenting stones into a patient. Shaft 206 can be rigid and formed from a metal or plastic material. In examples, shaft 206 can be sized for performing lithotripsy procedures in conjunction with an endoscope. As such, shaft 206 can be inserted into an incision in the epidermis of a patient, through a body cavity of the patient and into an organ. Thus, it is desirable for the diameter or cross-sectional shape of shaft 206 to be as small as possible to facilitate minimally invasive surgical procedures. However, shaft 206 can also incorporate a lumen to allow for removal, e.g., via suction, of fragments of stones produced by the fragmentation energy. As such, the size of shaft 206 and a lumen extending therethrough must be balanced to allow for minimal invasiveness and adequate removal of stone fragments. For example, too small of a lumen can increase the time it takes to fragment the stones into suitably small pieces. However, removal of stone fragments can be provided by a lumen within a delivery scope, such as working channel WC of endoscope E of FIG. 1.

With particular reference to FIG. 3, lid 234 of stone fragment canister 222 can be connected to a suction line of a lithotripsy device, such as collection tube 212 of FIG. 2. Suction pump 220 can include a pump device within housing 224 to produce a vacuum within container 232 to draw liquid and stone fragments from a lithotripsy device into container 232. Liquid and stone fragments within collection tube 212 can enter into container 232. The liquid and stone fragments can be deposited on the bottom of container 232. A filter or trap device within container 232 can prevent stone fragments from passing through container 232. A plurality of stone fragment canisters 222 can be strung together in series to collect fluid and stone fragments volumes larger than container 232 can provide. A user can set the level, magnitude or amount of suction generated by suction pump 220 using suction knob 228. Indicator 230 can provide an indication of the amount of suction being generated. Power switch 226 can be used to turn on or turn off electrical power being provided to the pump device within suction pump 220.

Cable 210 can provide electrical power to, and electronic communication means with handle 204. For example, cable 210 can provide electrical power to transducers within shaft 206 or nosecone 244 to provide energy for breaking up stones. Cable 210 can also conduct ultrasonic energy. Button 218A and button 218B can control operation of the transducer within shaft 206 or nosecone 244, such as by providing differing activation levels, e.g., power, to the transducer.

Collection tube 212 can be connected to barb 248 on handpiece 242. Barb 248 and collection tube 212 can be in fluid communication with the interior of shaft 206. Suction from suction pump 220 can be pulled through collection tube 212, barb 248 and shaft 206. Knob 219 can be rotated to control the amount of suction provided to shaft 206.

With particular reference to FIG. 4, in operation, hand 240 of a user can grasp or hold handpiece 242 with the thumb positioned toward knob 219 and button 218A and button 218B positioned proximate the fingertips. As such, the thumb can be used to push knob 219 back and forth to adjust the suction level, while the fingertips can be used to adjust the transducer power level. Additionally, hand 240 can be moved distally, e.g., in the direction of shaft 206, to engage the tip of shaft 206 with a stone. As such, the user can simultaneously control the suction level and activation energy while pushing shaft 206 into the stone. The level of force applied to the stone by shaft 206 is typically manually controlled by the user. Thus, a user typically utilizes skill and experience to determine how much force is being applied to the stone and how much force to apply to the stone. As discussed previously, the efficient transfer of energy from the transducers through shaft 206 can depend on the amount of force that shaft 206 applies to the stone. With the present disclosure, handle 204 can comprise a force indicator that can provide an indication of the amount of force that is being applied to the stone. Furthermore, the force indicators of the present disclosure can provide guidance as to whether or not the force being applied is inadequate, sufficient or excessive.

Figure 6:
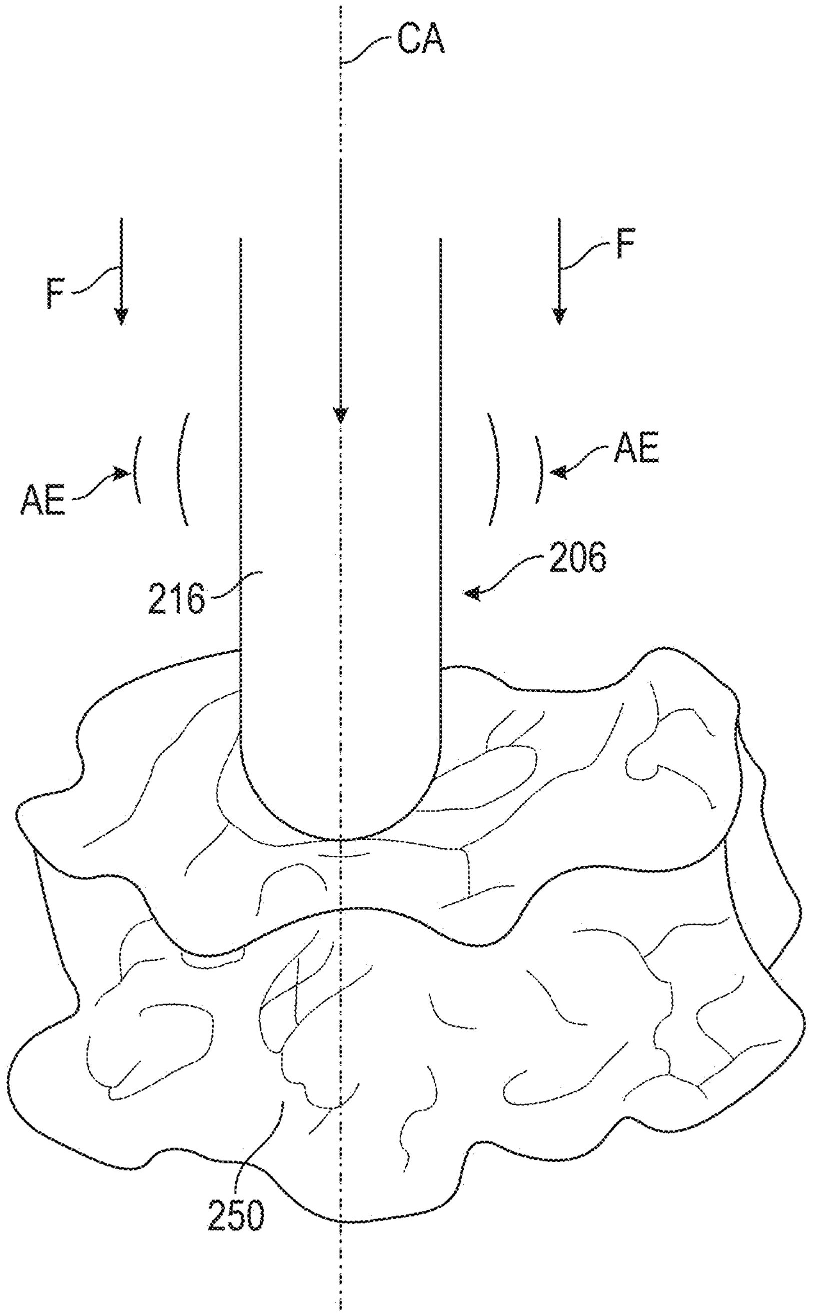
FIG. 6 is a schematic illustration of a lithotripsy shaft interacting with a stone.

FIG. 6 is a schematic illustration of shaft 206 interacting with stone 250. Distal end 216 of shaft 206 can be pushed into stone 250 by a user with force F. Distal end 216 can be configured to emit acoustic energy AE. If force F is insufficient, acoustic energy AE can be dissipated to the surroundings of stone 250 and not be transmitted to stone 250. If force Fis excessive, acoustic energy AE cannot properly exit from shaft 206 and can thus be muted or muffled relative to what is intended to be generated. Desirable or proper levels of force F can ensure that acoustic energy can leave shaft 206 and enter stone 250, thus adequately transferring from shaft 206 to stone 250. However, as mentioned, the ability of shaft 206 to engage stone 250 can depend on multiple factors, such as surgeon skill and experience, the amount that stone 250 is floating within the anatomy (e.g., the amount that stone 250 is immobilized in the anatomy by surrounding tissue, etc.), and the amount of suction being used to hold stone 250 in engagement with distal end 216. With the present disclosure, a force feedback device can be incorporated into lithotripsy system 200 to provide a user with indicia, e.g., visual, audio or tactile feedback, that can provide information relating to how well acoustic energy AE is being transmitted to stone 250. The indicia can provide concrete information to the user to allow for corrective action to be taken, thereby removing guesswork and estimating in applying force F with shaft 206.

Figure 7:
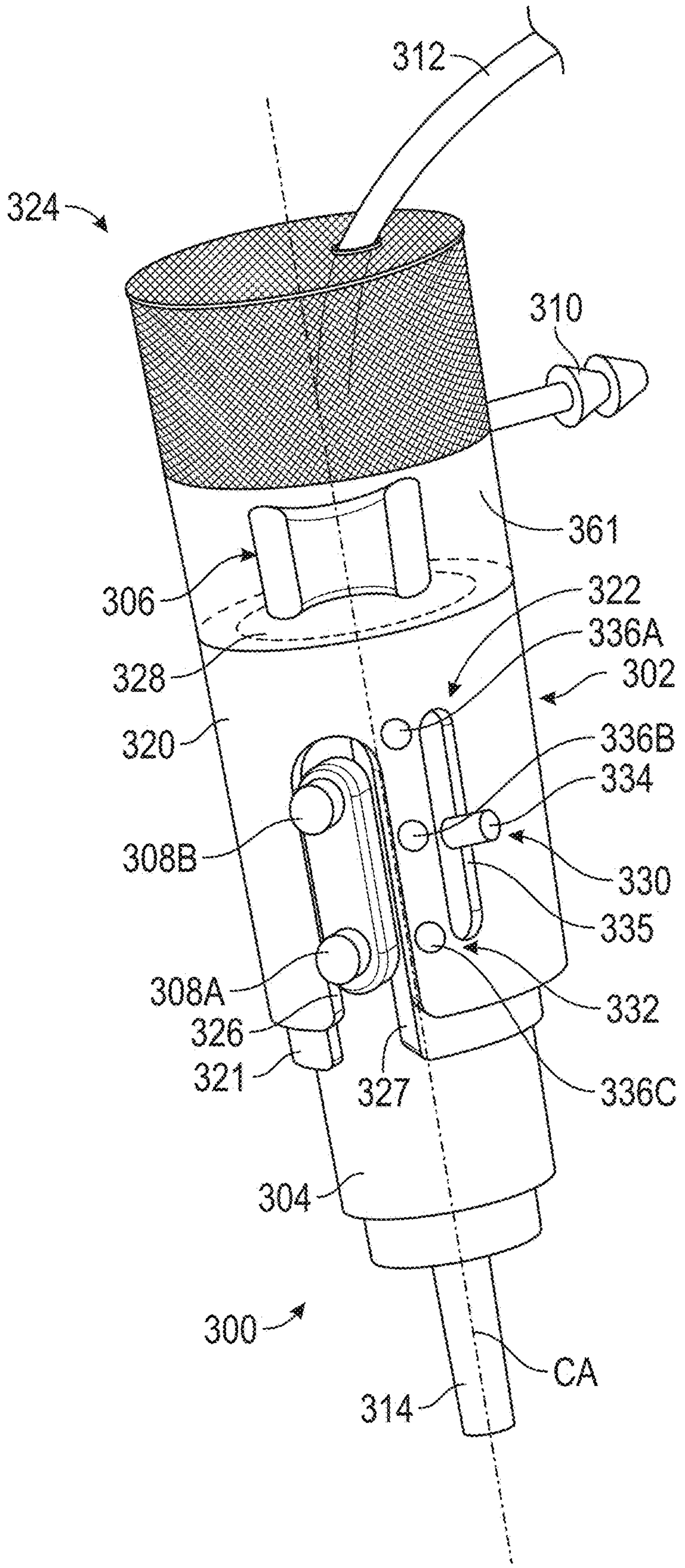
FIG. 7 is a perspective view of a handpiece of a lithotripsy device having a force indicator and a filter element of the present disclosure attached thereto.

FIG. 7 is a perspective view of lithotripsy device 300, which can comprise an example of hand-held probe 202 (FIG. 2), having force indicator device 302 of the present disclosure attached thereto. Lithotripsy device 300 can have handpiece 304 configured similarly as handle 204 of FIG. 2-FIG. 5. Suction knob 306 can be located at a proximal end of handpiece 304. Handpiece 304 can include button 308A and button 308B to control activation energy. Handpiece 304 can include barb 310 for connecting to a collection tube such as collection tube 212 (FIG. 2), and cable 312, which can comprise an example of cable 210. Shaft 314 can extend from handpiece 304 and can comprise an example of shaft 206.

Figure 10:
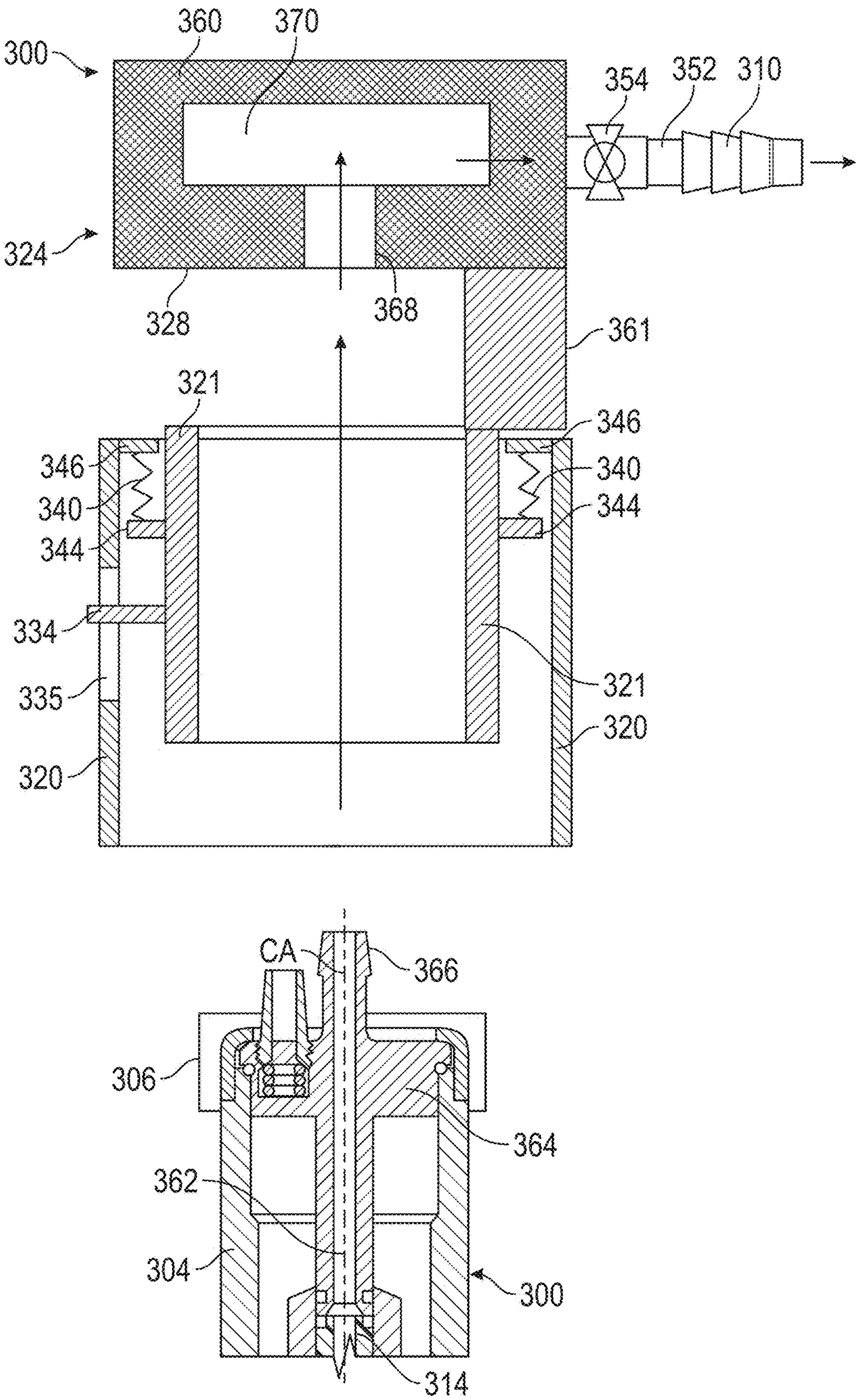
FIG. 10 is a schematic illustration showing a handpiece of a lithotripsy device positioned relative to a force indicating device of the present disclosure showing fluid flow through a filter element.

Force indicator device 302 can comprise slide 320, bracket 321 and force indicator 322. As can be seen in FIG. 10, bracket 321 can be configured as an add-on piece for handpiece 304 and slide 320 can be configured to surround and move relative to bracket 321. In examples, filter element 324 can be incorporated into force indicator device 302. Filter element 324 can comprise a body attached to or that is integral or monolithic with bracket 321. Filter element 324 can comprise a device configured to provide filtering of fluid passing into a distal end of handpiece 304 from a shaft (e.g., shaft 206 of FIG. 2) and exiting handpiece 304 proximally at barb 310. Force indicator device 302 can comprise indicator 330 and indicia 332. Indicator 330 can comprise peg 334 and slot 335. Indicia 332 can comprise first mark 336A, second mark 336B and third mark 336C. Peg 334 can be configured to move relative to slot 335 within slide 320. Peg 334 can comprise a post that is integral or monolithic with the material of bracket 321. In examples, peg 334 can be located on slide 320 and indicia 332 can be located on bracket 321. In additional examples, bracket 321 can be omitted and peg 334 can be included during manufacturing of handpiece 304, or can comprise an add-on feature as part of an upgrade feature for lithotripsy device 300 that can be attached to handpiece 304 via a threaded fastener, an interference fit within a bore, or chemical bonding means such as welding, adhesive or glue.

Bracket 321 can be configured as an add-on device for handpiece 304. That is, bracket 321 can be configured to be attached to and removed from handpiece 304 by a user. Bracket 321 can comprise a cylindrical body that can fit around handpiece 304. In example, bracket 321 can comprise a three-hundred-sixty-degree body that can be slid over an end of handpiece 304. In examples, bracket 321 can have a C-shaped cross-sectional profile to allow bracket 321 to be clipped onto a side of handpiece 304. Bracket 321 can attach to handpiece 304 to be immobilized relative thereto. As mentioned, in examples, bracket 321 can be omitted and peg 334 can be attached or otherwise extend directly from handpiece 304.

Slide 320 can comprise a cylindrical body that can fit around bracket 321. In example, slide 320 can comprise a three-hundred-sixty-degree body that can be slid over an end of bracket 321. In examples, slide 320 can have a C-shaped cross-sectional profile to allow slide 320 to be clipped onto a side of bracket 321. As mentioned, slide 320 can be configured to slide or translate along handpiece 304 without the use of bracket 321.

Slide 320 can comprise cut-out 326 and bracket 321 can include cut-out 327 to accommodate button 308A and button 308B. Additionally, opening 328 can be located on force indicator device 302, such as between bracket 321 and filter element 324 to accommodate suction knob 306. Bracket 321 can be connected to filter element 324 via extension 361.

Slide 320 can be configured to move relative to handpiece 304 and bracket 321. In particular, slide 320 can be configured to move relative to, e.g., slide axially along, bracket 321 relative to central axis CA. Slide 320 can comprise a gripping feature for the user of lithotripsy device 300. Thus, by gripping slide 320, the functions of lithotripsy device 300 can be controlled and shaft 314 can be pushed into a stone.

In use, slide 320 can be grasped by a user similarly as described with reference to handpiece 242 of FIG. 4. Thus, a thumb can be positioned proximate to suction knob 306 and fingertips can be positioned proximate button 308A and button 308B. The palm of the hand can be placed around slide 320. As a user pushes down on slide 320, handpiece 304 can apply downward force F (FIG. 6) with shaft 314.

Handpiece 304 can move upward (relative to the orientation of FIG. 7) relative to slide 320 along central axis CA, which can cause peg 334 to move within slot 335. Peg 334 can therefore, additionally move relative to first mark 336A, second mark 336B and third mark 336C. In examples, peg 334 can start out at one end of slot 335 and can move toward the other end of slot 335 as more downward force is applied to slide 320. Thus, in examples, peg 334 can start proximate third mark 336C, and third mark 336C can convey that insufficient force is being applied, second mark 336B can convey that adequate force is being applied, and first mark 336A can convey that too much force is being applied. As discussed in greater detail below with reference to FIG. 8, lithotripsy device 300 can include one or more of a biasing element, e.g., biasing element 340, to provide resistance to the movement of slide 320 relative to handpiece 304 and a force sensor, e.g., sensor 342, to determine the amount of force being applied to slide 320.

Figure 8:
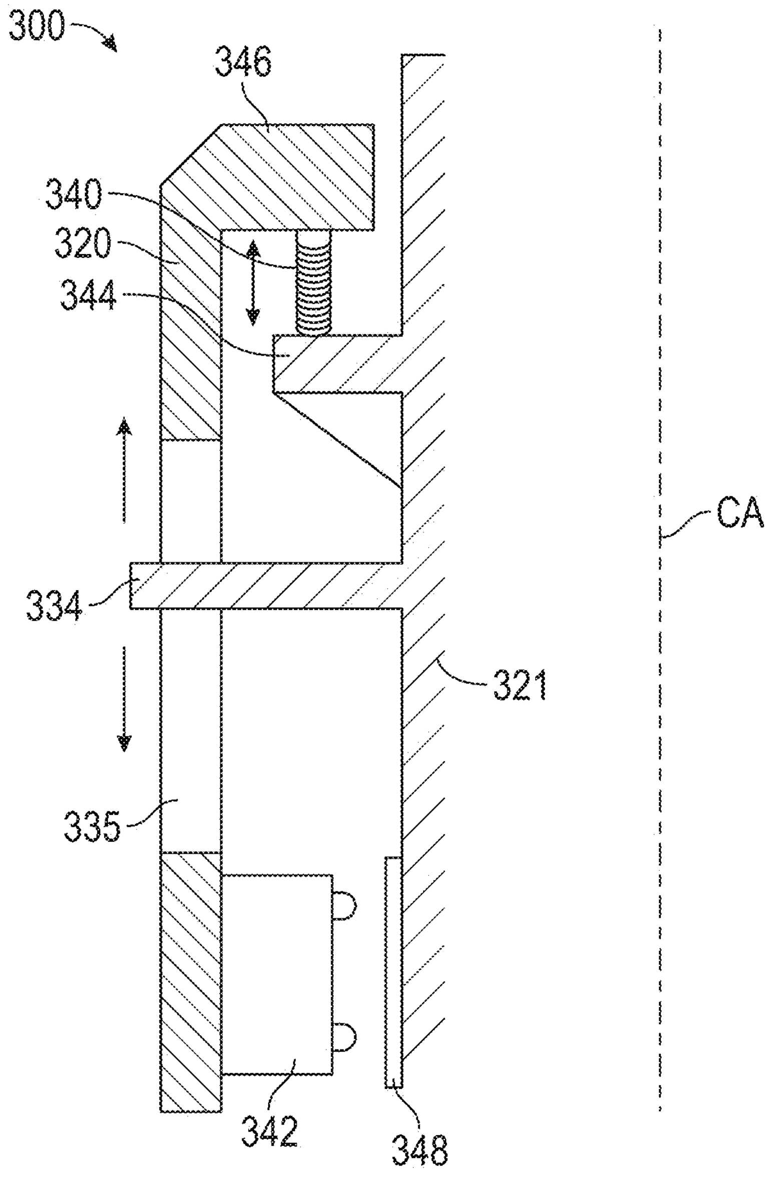
FIG. 8 is a partial cross-sectional view of the lithotripsy handle and the force control device of the present disclosure illustrating a biasing element and a force indicator located in a slot.

FIG. 8 is a partial cross-sectional view of lithotripsy device 300 showing slide 320, bracket 321, biasing element 340 and sensor 342.

Slide 320 can be disposed about bracket 321. As discussed, each component can comprise a cylindrical body surrounding central axis CA. Slide 320 can be configured to be displaced or move axially relative to central axis CA along bracket 321. In examples, slide 320 can be free-floating relative to bracket 321 and connected thereto by biasing element 340. In examples, slide 320 can be attached to bracket 321 to allow slide 320 to slide against bracket 321. For example, bracket 321 and slide 320 can include a rail system (not illustrated) to allow slide 320 to slide axially relative to central axis CA and prevent rotation about central axis CA. In example, bracket 321 can comprise one or more longitudinally extending slots having a dovetail cross-section recessed therein and slide 320 can have one or more longitudinally extending rails having a dovetail cross-section that mates with the slots.

Biasing element 340 can be positioned between slide 320 and bracket 321 to bias slide 320 to a first position, such as a starting position. In particular, bracket 321 can include flange 344 and slide 320 can include lip 346 between which biasing element can be positioned, thereby allowing biasing element 340 to provide an indication of the amount of longitudinal or axial force that is being applied by shaft 314, relative to the central axis of shaft 314. In examples, a single flange 344 and a single lip 346 can be included for a single instance of biasing element 340. In additional examples, multiple instances of flange 344 and lip 346 and biasing element 340 can be spaced around the circumference of lithotripsy device 300 about central axis CA for engagement with multiple biasing elements 340, as shown in FIG. 10. In additional examples, flange 344 and lip 346 can extend completely around handpiece 304 and slide 320, e.g., can form three-hundred-sixty-degree shelves. In example, biasing element 340 can be configured to push slide 320 upward away from shaft 314 such that downward movement of slide 320 by a user will compress or shrink the length or height of biasing element 340. In examples, biasing element 340 can comprise a coil spring or a compression spring as illustrated. In additional examples, biasing element 340 can comprise a tension spring wherein movement of slide 320 is configured to elongate or stretch the compression spring. For example, biasing element 340 could disposed between flange 344 and peg 334. In additional examples, biasing element 340 can comprise a disk spring, an air piston or other variable stiffness devices. In additional examples, biasing element can comprise one or more pieces of a compressible or stretchable material, such as foam, rubber or a compressible polymer. Such pieces of compressible material can have a ring or donut shape. In examples, biasing element 340 or another biasing element can be configured to provide an indication of the amount of lateral or radial force applied by shaft 314, relative to the central axis of shaft 314. For example, biasing element could be positioned to extend radially from bracket 321 to engage slide 320.

The compressed and stretched lengths of biasing element 340, the length of slot 335 and the spring force of biasing element 340 can be selected to provide feedback as to how much force is being applied to slide 320. Thus, for example, biasing element 340 being compressed zero percent can correspond to when no force is being applied to slide 320, biasing element 340 being fully compressed can correspond to when a force that exceeds any desired force that should be applied to a physiological calculi or stone is being applied to slide 320, and biasing element 340 being halfway compressed can correspond to when a desired force is being applied to fracture the stone an adequate amount, e.g., a desired level of force F (FIG. 6) is applied to stone 250 to allow ultrasonic energy to be efficiently transmitted therebetween. Empirical testing can be conducted to determine the appropriate configurations of biasing element 340, the length of slot 335 and the spring force of biasing element 340. In additional examples, biasing element 340 can be configured to be capable of elastic deflection without permanent deformation, such as metals. In examples, biasing element 340 can be configured as a cart spring type structure.

In examples, biasing element 340 can be configured to push slide 320 upward with reference to the orientation of FIG. 7 and FIG. 8. Thus, third mark 336C can comprise a yellow mark indicating insufficient force, second mark 336B can comprise a green mark indicating appropriate force, and first mark 336A can comprise a red mark indicating excessive force. In examples, first mark 336A, second mark 336B and third mark 336C can comprise mechanical indicators, such as paint or stickers applied to slide 320. First mark 336A, second mark 336B and third mark 336C can have various shapes, such as circles, squares, rectangles, octagons, hexagons and the like. Each of these shapes can be small so as to form a spot or dot on slide 320.

In examples, first mark 336A, second mark 336B and third mark 336C can comprise a light emitter, such as a light emitting diode (LED) or a light bulb. For example, first mark 336A-third mark 336C can be configured as indicia 406A-indicia 406E of FIG. 11.

In additional examples, force indicator device 302 can be configured to provide audio feedback. In such examples, force indicator device 302 can include an output device, such as a speaker. For example, force indicator device 302 can include audio driver 404 of FIG. 11.

In examples, force indicator device 302 can be configured to provide tactile feedback. In such examples, force indicator device 302 can include an output device, such as a motor. For example, force indicator device 302 can haptic motor 409 of FIG. 11.

In examples, indicia 332 can provide written text or indicia to convey additional information or instructions for a user. For example, indicia 332 can be configured to provide feedback regarding different breakage levels to be applied to a stone. For example, first mark 336A can provide feedback indicating a "fracture" level of force to be applied to the stone to break the stone into smaller pieces, while third mark 336C can provide feedback indicating a "pulverize" level of force to be applied to the stone to break the stone into powder, and second mark 336B can provide an intermediate level of force.

In examples, indicia 332 can be configured to provide feedback regarding adequate level of force to be applied to different types of stones. For example, kidneys stones can comprise calcium stones, struvite stones, uric acid stones and cystine stones. These stones can have different levels of hardness that correspondingly can benefit from different levels of force to fragmentize or break apart. Thus, first mark 336A can include indicia indicating "calcium stone" to provide feedback indicating force to be applied to break a calcium stone into smaller pieces, second mark 336B can include indicia indicating "struvite stone" to provide feedback indicating force to be applied to break a struvite stone into smaller pieces, and third mark 336C can include indicia indicating "uric acid stone" to provide feedback indicating force to be applied to break a uric acid stone into smaller pieces. Empirical testing can be conducted to arrange the stone label indicia in the appropriate order of hardness corresponding to the operation of biasing element 340. For example, harder stones can be listed where biasing element 340 is compressed more.

In examples, sensor 342 can be used to obtain electronic feedback from lithotripsy device 300. Specifically, sensor 342 can be used to obtain electronic feedback from lithotripsy device 300 relating to the amount of force being applied by shaft 314 to stone 250 (FIG. 6), which corresponds to the amount of force being applied to slide 320 by a user. Sensor 342 can be configured to engage with readable feature 348. In examples, sensor 342 can comprise a limit switch that can sense the location of slide 320 relative to bracket 321. Thus, sensor 342 can be configured to mechanically engage with readable feature 348 of bracket 321 comprising projections. In examples, sensor 342 can be configured as a roller lever sensor or a plunger sensor and bracket 321 can include a pair of projections, similar to peg 334 but shorter, to engage with the limit switch in two positions. Sensor 342 can also be configured to obtain location information from bracket 321 via electronic means, wireless means or non-contact means. In examples, sensor 342 can be configured as a magnetic position sensor and readable feature 348 can include one or more pieces of magnetic material to engage with the magnetic position sensor in different positions of slide 320. In examples, sensor 342 can be configured as a capacitance position sensor and readable feature 348 can include one or more pieces of capacitance-hanging material, such as aluminum, tantalum, ceramic and polycarbonates, to engage with the magnetic position sensor in different positions of slide 320. In examples, sensor 342 can be configured as an encoder and readable feature 348 can include a track having hashmarks or graduation marks that can be read by the encoder, thereby allowing the encoder to count the marks as slide 320 is translated along bracket 321. Output of sensor 342 can be processed by electronics to provide indicia or feedback to a user, as is discussed in greater detail with reference to FIG. 11.

Figure 9:
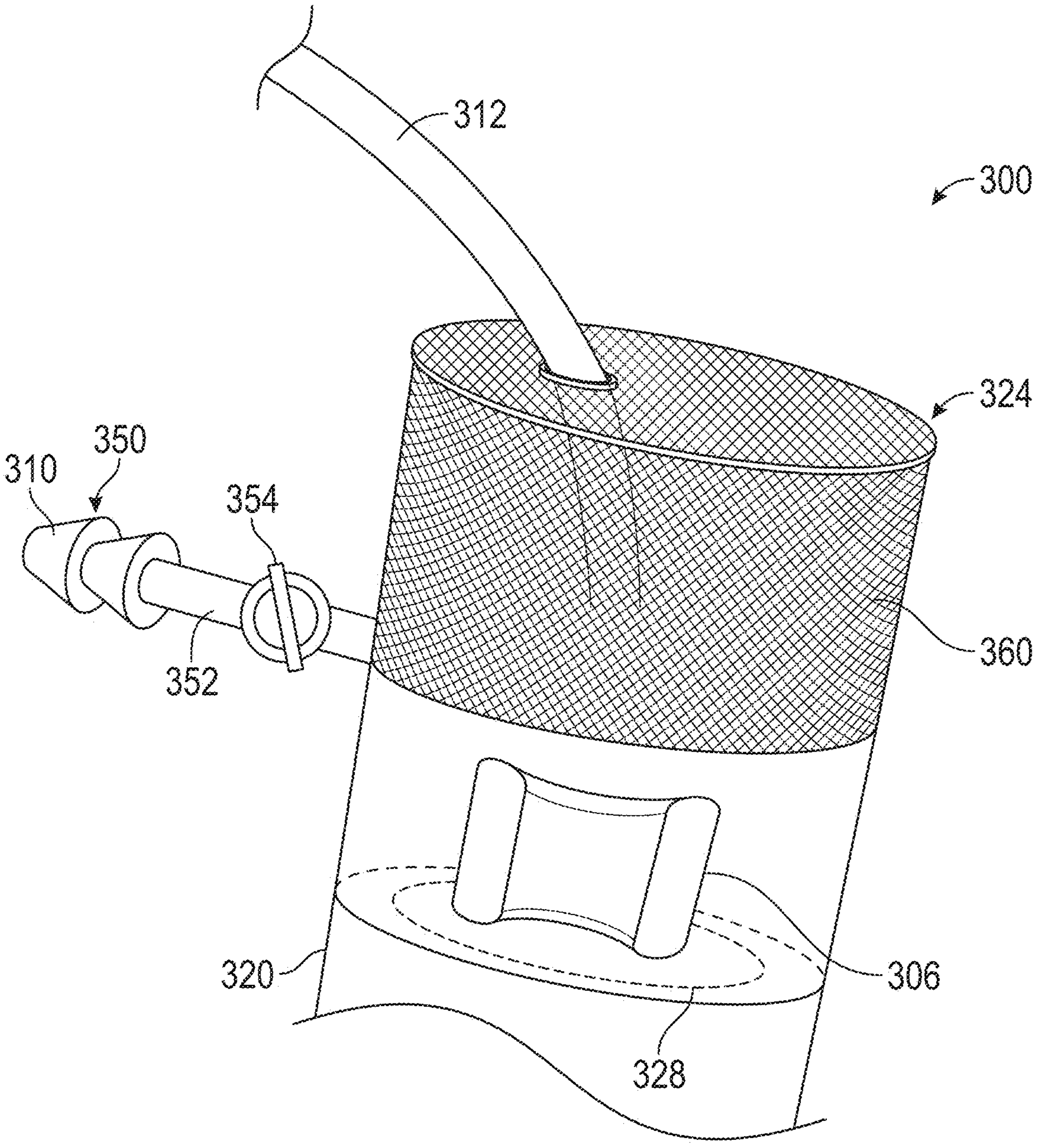
FIG. 9 is a perspective view of a handpiece of a lithotripsy device having an outflow controller of the present disclosure connected to a filter element.

FIG. 9 is a perspective view of force indicator device 302 for lithotripsy device 300 having outflow controller 350 of the present disclosure connected to filter element 324. Outflow controller 350 can comprise stem 352, valve 354 and barb 310. Filter element 324 can comprise filter body 360. FIG. 10 is a schematic illustration showing handpiece 304 of lithotripsy device 300 positioned relative to force indicating device 302 of the present disclosure showing fluid flow through filter element 324. FIG. 9 and FIG. 10 are discussed concurrently.

Filter element 324 can be positioned on slide 320 to fluidly position filter body 360 between fluid passage 362 within shaft 314 and a passage for stone fragment canister 222, such as barb 310. Filter element 324 can be connected to slide 320 by extension 361. As discussed herein, suction pump 220 can apply a vacuum force to shaft 314 to pull fluid and stone fragments into fluid passage 362. The fluid and stone fragments can flow from shaft 314, through cap 364 and into outlet barb 366. After leaving lithotripsy device 300, the fluid and stone fragments can pass into filter element 324. In the illustrated example, filter element 324 is attached directly to handpiece 304 of lithotripsy device 300 at outlet barb 366. Thus, outlet barb 366 can be inserted into socket 368 in filter element 324. However, tubing can be positioned between outlet barb 366 and socket 368. Filter body 360 can be disposed within a waterproof housing of filter element 324 to prevent fluid and stone fragments from passing through filter element 324 other than at barb 310. Filter body 360 can comprise a material that allows fluid to pass therethrough but that prevent solids from passing therethrough. In examples, filter body 360 can comprise foam, a wire mesh, cellulose filter material, a polypropylene membrane or the like. Filter body 360 can form pocket 370 in which stone fragments can be captured. Thus, fluid and stone fragments can flow into pocket 370 from socket 368 and fluid can flow through filter body 360 into stem 352 while stone fragments remain in pocket 370. Barb 310 can be positioned at the distal end of stem 352 to allow for coupling to a hose, such as collection tube 212 of FIG. 2. Thus, filter element 324 can prevent collection tube 212 (FIG. 2) from becoming clogged with stone fragments. Valve 354 can be positioned in stem 352 to provide a means for controlling flow out of stem 352, e.g., through lithotripsy device 300. Valve 354 can comprise an on/off valve or a valve that allows intermediate levels of flow between on and off. In examples, valve 354 can comprise a needle valve, a ball valve, a butterfly valve and the like. Valve 354 can be manually operated by a user of lithotripsy device 300 to control the amount of suction being applied at the distal end of shaft 314 at fluid passage 362. Valve 354 can be used alternatively to suction knob 306. In examples, slide 320 can be configured to disable suction knob 306. Thus, a user of indicator device 302 can be provided with the ability to control suction even if suction knob 306 is interfered with by slide 320, such as in examples where opening 328 is omitted.

Figure 11:
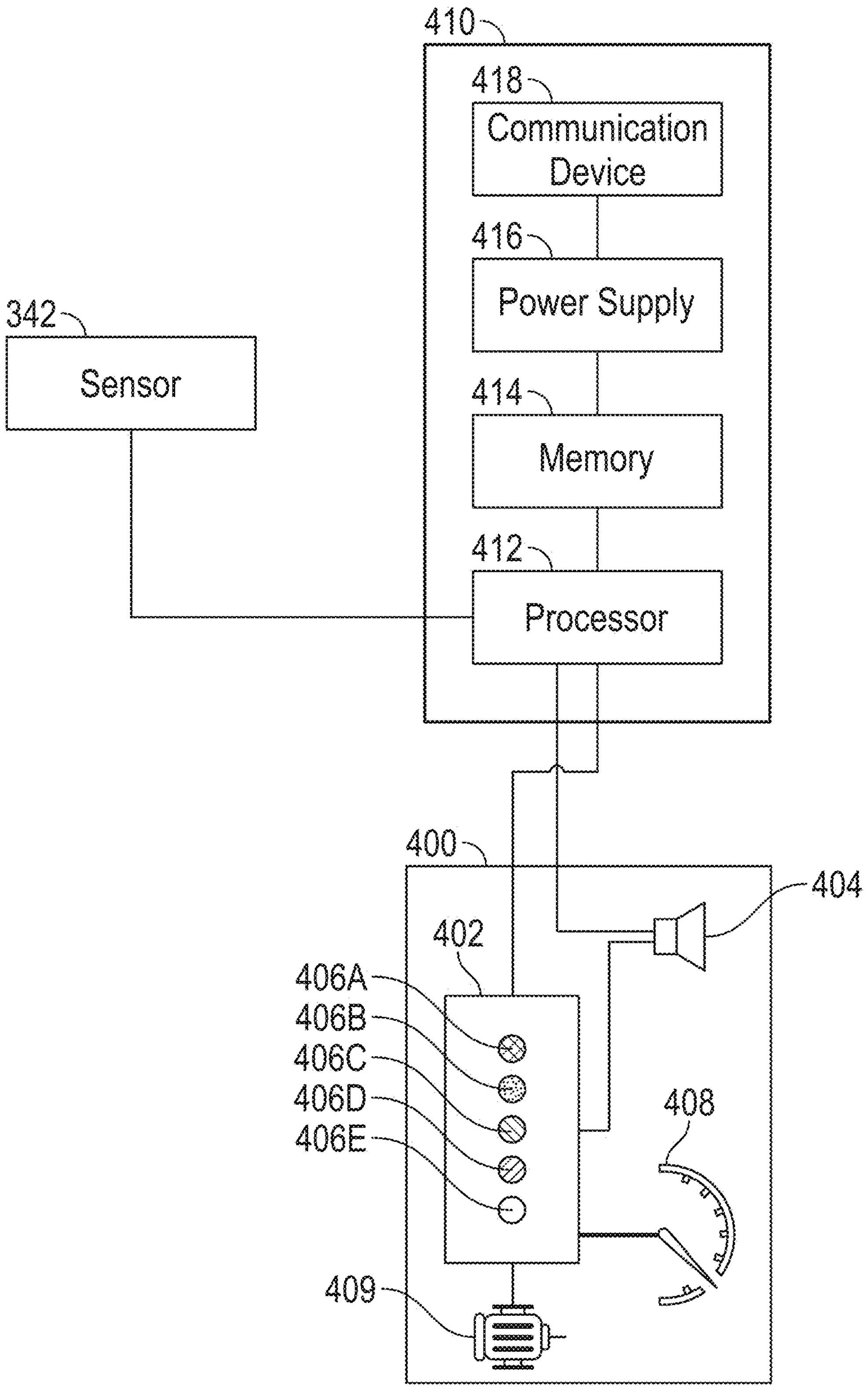
FIG. 11 is a schematic view of an output device suitable for use with the force indicator devices of the present disclosure.

FIG. 11 is a schematic view of output device 400 suitable for use with force feedback devices disclosed herein. Output device 400 can comprise visual display 402 and audio driver 404. Visual display 402 can comprise output indicia 406A-output indicia 406E, dial 408 and haptic motor 409. Output device 400 can comprise, or can be in communication with, electronics module 410. Electronics module 410 can comprise processor 412, memory 414, power supply 416 and communication device 418. Processor 412 can be in communication with sensor 342.

In examples, sensor 342 can be in communication with output device 400 via electronics module 410. In examples, sensor 342 can be in direct communication with output device 400.

In examples, output device 400 and electronics module 410 can be located on or in force indicator device 302 (FIG. 7). Thus, force indicator device 302 can comprise a self-contained device. In examples, output device 400 and electronics module 410 can be located on or in generator console 208 (FIG. 2). Thus, force indicator device 302 can comprise a communication device, such as communication device 418 without the other components of electronics module 410, such as a wireless transmitter or a wired connection, to communicate output of sensor 342 with generator console 208.

Visual display 402 can comprise an active display unit, such as a liquid crystal display, a plasma screen, an organic light-emitting diode display and the like. Visual display 402 can comprise a touchscreen device. In examples, processor 412 can comprise or be part of generator console 208 (FIG. 2). As such, visual display 402 can be programmed to provide a variety of outputs and receive a variety of user-inputs. As described herein, sensor 342 can comprise a location sensor, a presence sensor, a proximity sensor and the like. Memory 414 can include information related to indicia and instructions to be displayed on visual display 402, such as force magnitude, force adequacy, desired fracture level, stone type and the like. Thus, processor 412 can receive an input from sensor 342, consult a lookup table stored in memory 414 to find an output indicia for the corresponding output of sensor 342 and display on visual display 402 or provide another feedback output the magnitude of the force, the adequacy of the force, a type of stone suitable for use with the force and the like. Activation of at least one of indicia 406A-indicia 406E, as well as audio driver 404, dial 408 and haptic motor 409, can provide an indication of force, pressure, stone type, breakage function (e.g., fracture or pulverize) and the like. With respect to FIG. 11, for example, indicia 406A-indicia 406E can be responsive to electrical or mechanical parameters sensed by sensor 342.

In examples, each of indicia 406A-indicia 406E can be activated to indicate a progressively larger magnitude or level of force. Each of indicia 406A-indicia 406E can comprise a light emitting diode. In examples, indicia 406E at the bottom of output device 400 and indicia 406A at the top of output device 400 can be activated in opposite manners to indicate opposite ends of a force application spectrum. Thus, indicia 406E can be activated to show a first level of a force, such as a magnitude of the force that shaft 314 or distal end 216 of shaft 206 is applied to stone 250 (FIG. 5) just above zero, and indicia 406A can be activated to show a second level of a force, such as a magnitude of the force that shaft 314 or shaft 206 is applied to stone 250 at a maximum or threshold level. Indicia 406B, indicia 406C and indicia 406D can be activated to indicate varying levels in between the first and second levels such that a continuous spectrum or a gradual changing of light emitting activation can be provided. Indicia 406A-indicia 406E can update in real-time to indicate the magnitude of the force. Thus, as a surgeon manipulates lithotripsy device 300 to engage shaft 314 with stone 250, an indication of the amount of force that shaft 314 is applying to stone 250 can be provided. In other examples, all of indicia 406A-indicia 406E can be activated, or lit up, and can change colors to indicate the magnitude of the electrical parameter. For example, lighter colors can be used to indicates lower force applied and darker colors can be sued to indicate higher force applied.

In examples, indicia 406A-indicia 406E and dial 408 can be provided with labels to translate the magnitudes of the sensed applied force into anatomical descriptions. For example, high levels of force can be translated into a first type of stone and low levels of force can be translated into a second type of stone.

In examples, indicia 406A-indicia 406E and dial 408 can be provided with labels to translate the magnitudes of the sensed applied force into a fragmentation descriptions. For example, high levels of force can be translated into a first type of fragmentation, e.g., fracture, and low levels of force can be translated into a second type of fragmentation, e.g., powdered.

In an example, visual display 402 can include dial 408. Dial 408 can include a scale to indicate different magnitudes of the force and a needle can move to indicate the magnitude being actively applied.

In examples, an audible alarm can be used to provide feedback indicating the magnitude of the applied force, such as by using audio driver 404. For example, a steady signal can be emitted that changes pitch, volume or tone based on the magnitude of the sensed force. In other examples, an intermittent signal can be emitted that changes intervals based on the magnitude of the applied force.

In examples, a tactile alarm can be used to provide feedback indicating the magnitude of the applied force, such as by using haptic motor 409. For example, a steady vibration can be emitted that changes speed, e.g., frequency, based on the magnitude of the sensed force. In other examples, an intermittent signal can be emitted that changes intervals based on the magnitude of the applied force.

Figure 12:
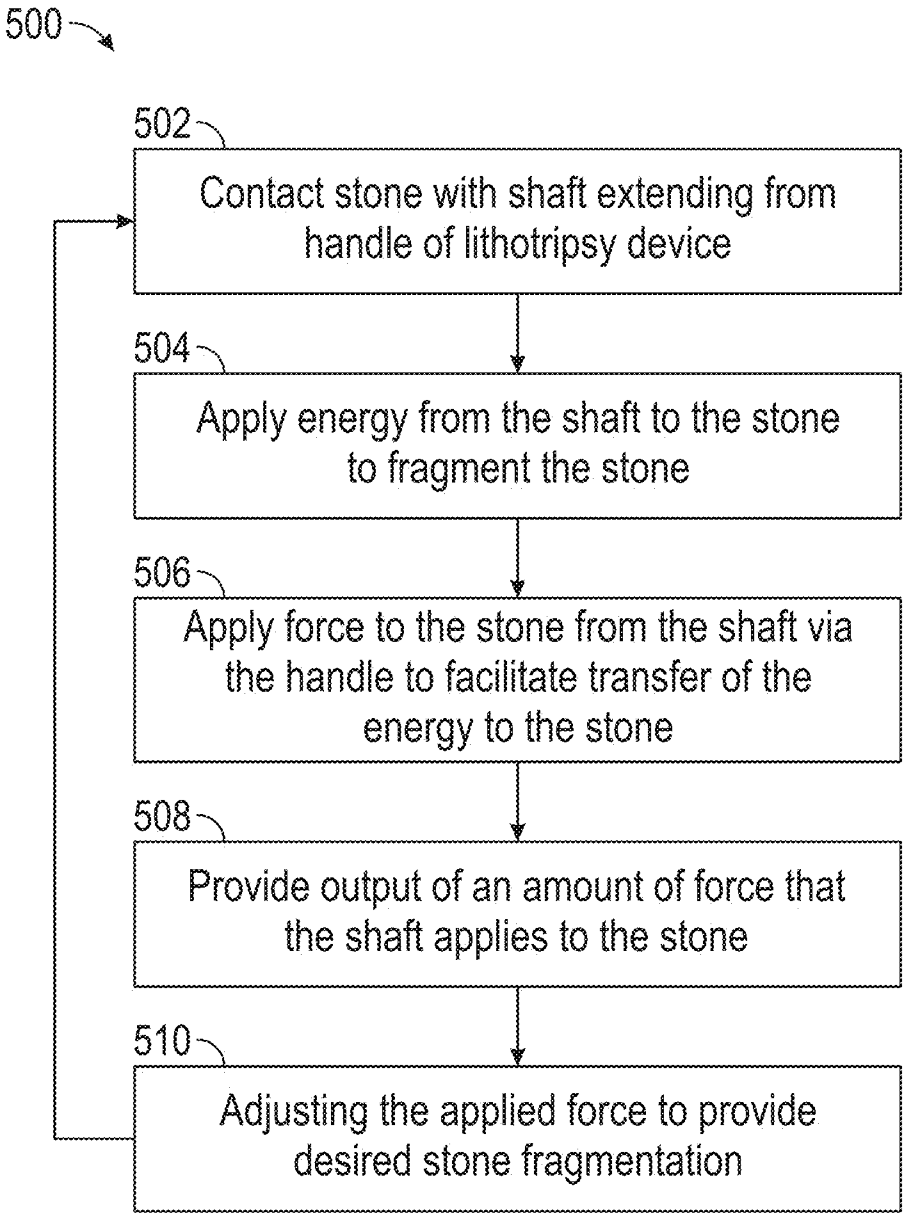
FIG. 12 is a block diagram illustrating method for determining force applied with a lithotripsy device during a lithotripsy procedure using the devices of the present disclosure.

FIG. 12 is a line diagram illustrating method 500 for applying fragmentation force to a stone using a lithotripsy system of the present disclosure including a force feedback device. Method 500 illustrates various exemplary operations of a stone fragment process. Other operations as described herein can be included and some steps can be omitted. Additionally, the illustrated and described operations can be performed in different orders.

At operation 502, a shaft extending from handle of lithotripsy device can contact a physiological calculi or stone. For example, shaft 314 of lithotripsy device 300 (FIG. 7) can be applied to stone 250 (FIG. 6). Shaft 314 can be inserted into anatomy of a patient to reach a stone. In examples, shaft 314 can be inserted through working channel WC of scope E (FIG. 1).

At operation 504, energy from the shaft can be applied to the stone to fragment the stone. In examples, acoustic can be emitted from shaft 314. Acoustic energy can include sound waves, sonic waves, ultrasonic waves or shock waves, or any combination of these. Additionally, shaft 314 can be configured to emit pneumatic lithotripsy, electro-hydraulic lithotripsy (EHL), and laser lithotripsy including dissolution of calculi using green light, YAG, or holmium lasers. The stone fragmentation energy can be generated within lithotripsy device 300 within handpiece 304 or shaft 314, or can be generated within signal generator 116 (FIG. 1). The stone fragmentation energy can be configured to be emitted from the distal end of shaft 314, similar to distal end 216 of shaft 206. As discussed herein, the stone fragmentation energy can be transmitted through shaft 314 and can pass through the material of shaft 314. Thus, it is desirable to engage shaft 314 with stone 250, e.g., make contact between shaft 314 and stone 250.

At operation 506, force from the shaft can be applied to the stone via the handle to facilitate transfer of the energy to the stone. A user can push down on handpiece 304 to push shaft 314 into stone 250. In particular, a user can push down on slide 320 of indicator device 302 to transmit force to handpiece 304 through biasing element 340 and bracket 321. Downward force on handpiece 304 can cause shaft 314 to be pushed into stone 250. As the force applied to slide 320 exceeds the spring force of biasing element 340, assuming stone 250 is sufficiently immobilized within the anatomy, biasing element 340 can begin to activate, e.g., compress or expand depending on the arrangement. Activation of biasing element 340 can cause relative displacement between slide 320 and bracket 321, including handpiece 304. The relative movement between slide 320 and bracket 321 can be used to determine an amount of force being applied to handpiece 304 by a user.

At operation 508, an amount of force that the shaft applies to the stone can be output. The output can comprise indicia that ensures a suitable amount of fragmentation energy is being generated by or passing through shaft 314 and transmitted to stone 250 to provide a desired outcome. For example, the desired outcome can be to fragment the stone as efficiently as possible to reduce procedure time and to break the stone into small pieces quickly. Thus, it can be desirable to allow the most amount of fragmentation energy coming from shaft 314 to be passed to stone 250. This scenario can benefit from shaft 314 engaging stone 250 at an optimal level, e.g., with not too much force to prevent shaft 314 from being dampened (e.g., prevent the generation of fragmentation energy) and with not too little force to ensure transmission of the fragmentation energy to stone 250. However, in some cases it can be desirable to have less fragmentation energy be emitted from shaft 314, to, for example, break the stone into larger pieces or break-up softer stone types. This scenario can benefit from shaft 314 engaging stone 250 less than or more than optimally to reduce the generation or transmission of fragmentation energy.

The amount of force that the distal tip of shaft 314 applies to stone 250 can be output in a format readable by a human. In additional examples, the amount of lateral or radial force applied by shaft 314 to stone 250 can be output. In examples, the output can be directly readable by a human, such as by the use of a mechanical indicator, such as indicator 330 and indicia 332. In examples, the output can be indirectly readably by a human, such as by the use of electronics module 410 to convert electrical output of sensor 342 to electronic means viewable (visual), hearable (audible) or feelable (tactile) by a human. Additionally, the force output can be converted to instructions for adjusting the force output. In examples, the instructions can provide human readable indicia for applying more or less force, desirable amount of force for certain stone types or desirable amount of force for different fragmentation levels.

At operation 510, the applied force from the shaft can be adjusted to provide desired stone fragmentation. For example, a user can adjust the amount of force manually being applied to handpiece 304 via slide 320. A user can increase downward force on slide 320 to provide more force against stone 250. A user can decrease downward force on slide 320 to provide less force against stone 250. The amount of applied force can be directly proportional to the amount of fragmentation energy that is imparted to stone 250, thereby corresponding to how fast stone 250 is broken or how small of fragments that stone 250 is broken into.

The present disclosure addresses the issue of kidney stone fragments clogging the suction system during lithotripsy, causing procedural downtime and potential device repair or replacement. The present disclosure provides a force indicating device that helps a user apply the correct amount of force to a kidney stone in order to facilitate desirable transmission of fragmentation energy, e.g., acoustic energy, from a lithotripter shaft to the stone. The feedback can provide an indication of force level or magnitude, instructions for applying more or less force, and instructions for applying force to different types of stones.

Various Notes and Examples

For the purposes of this disclosure, "proximal" refers to an end of the system that is closer the device operator during use, and "distal" refers to an end of the system that is distal, or further from the device operator during use.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

Example 1 is a feedback device for providing force indicia generated during a lithotripsy procedure, the feedback device comprising: a slide configured to attach to a handpiece of a lithotripsy device; a positioning device connected to the slide to adjust a position of the slide relative to the handpiece; and a feedback indicator connected to the slide to provide feedback related to a force being applied to the slide to displace the slide relative to the handpiece.

In Example 2, the subject matter of Example 1 optionally includes wherein: the positioning device comprises a biasing element; and the feedback indicator produces feedback related to a relative position of the slide relative to the handpiece.

In Example 3, the subject matter of any one or more of Examples 1-2 optionally include wherein the feedback indicator comprises at least one of a visual output indicator, an audio output indicator or a haptic output indicator.

In Example 4, the subject matter of Example 3 optionally includes wherein the feedback indicator further comprises: a sensor configured to determine a relative position between the slide and the handpiece.

In Example 5, the subject matter of any one or more of Examples 1~4 optionally include wherein: the handpiece comprises a suction knob and an energy button; and the slide comprises one or more cut-outs through which the suction knob or the energy button extend to allow the slide to fit onto the handpiece.

Example 6 is a lithotripsy system comprising: a handpiece configured to be held by a user; an energization source configured to generate an energy for breaking apart a physiological calculi; a shaft having a proximal end extending from the handpiece and a distal end configured to engage the physiological calculi; and a force indicating device connected to the handpiece, the force indicating device configured to provide feedback related to a force that is being applied to the physiological calculi by the distal end of the shaft by a user at the handpiece.

In Example 7, the subject matter of Example 6 optionally includes wherein the force indicating device comprises: a slide moveable relative to the handpiece; an indicator post mounted to one of the slide and the handpiece; and indicia located on the other of the slide and the handpiece; wherein the indicator post is movable relative to the indicia to provide the feedback.

In Example 8, the subject matter of Example 7 optionally includes wherein the force indicating device further comprises a spring disposed to resist movement of the slide.

In Example 9, the subject matter of any one or more of Examples 7-8 optionally include wherein the feedback comprises: a first visual indicator on the handpiece denoting excessive force; and a second visual indicator on the handpiece denoting inadequate force; wherein a desired force range is indicated when the indicator post is positioned between the first visual indicator and second visual indicator.

In Example 10, the subject matter of Example 9 optionally includes wherein the first visual indicator and the second visual indicator are colored shapes or LED lights.

In Example 11, the subject matter of any one or more of Examples 6-10 optionally include wherein the feedback comprises haptic feedback based on the applied force.

In Example 12, the subject matter of any one or more of Examples 6-11 optionally include a filter connected to the handpiece.

In Example 13, the subject matter of any one or more of Examples 6-12 optionally include an outflow controller on the handpiece configured to control a suction flow rate through the shaft.

Example 14 is a method of performing a lithotripsy procedure, the method comprising: contacting a stone with a shaft extending from a handle of a lithotripsy device; applying energy from the shaft to the stone to fragment the stone; applying a force to the stone from the shaft via the handle to facilitate transfer of the energy to the stone; and providing an output of an amount of force that the shaft contacts the stone.

In Example 15, the subject matter of Example 14 optionally includes adjusting the applied force based on the output.

In Example 16, the subject matter of Example 15 optionally includes wherein the output comprises visual output.

In Example 17, the subject matter of Example 16 optionally includes determining if the applied force is within a desired range between a first visual indicator and a second visual indicator denoting excessive and inadequate force, respectively.

In Example 18, the subject matter of any one or more of Examples 14-17 optionally include wherein the output comprises haptic feedback related to the applied force.

In Example 19, the subject matter of any one or more of Examples 14-18 optionally include wherein the output comprises audio feedback related to the applied force.

In Example 20, the subject matter of any one or more of Examples 14-19 optionally include wherein the output comprises indicia indicating different types of stones.

In Example 21, the subject matter of any one or more of Examples 14-20 optionally include wherein the energy comprises ultrasonic energy, laser energy, ultrasound energy, pneumatic or hydraulic energy.

Each of these non-limiting examples can stand on its own, or can be combined in various permutations or combinations with one or more of the other examples.

What is claimed is:

1. A lithotripsy system comprising:

a handpiece configured to be held by a user;

an energization source configured to generate an energy for breaking apart a physiological calculi;

a shaft having a proximal end extending from the handpiece and a distal end configured to engage the physiological calculi; and a force indicating device connected to the handpiece, the force indicating device configured to provide feedback related to a force that is being applied to the physiological calculi by the distal end of the shaft by a user at the handpiece; wherein the force indicating device comprises:

a slide moveable relative to the handpiece;

an indicator post mounted to one of the slide and the handpiece; and indicia located on the other of the slide and the handpiece;

wherein the indicator post is movable relative to the indicia to provide the feedback.

2. The lithotripsy system of claim 1, wherein the force indicating device further comprises a spring disposed to resist movement of the slide.

3. The lithotripsy system of claim 1, wherein the feedback comprises:

a first visual indicator on the handpiece denoting excessive force; and a second visual indicator on the handpiece denoting inadequate force;

wherein a desired force range is indicated when the indicator post is positioned between the first visual indicator and second visual indicator.

4. The lithotripsy system of claim 3, wherein the first visual indicator and the second visual indicator are colored shapes or LED lights.

5. The lithotripsy system of claim 1, wherein the feedback comprises haptic feedback based on the applied force.

6. The lithotripsy system of claim 1, further comprising a filter connected to the handpiece.

7. The lithotripsy system of claim 1, further comprising an outflow controller on the handpiece configured to control a suction flow rate through the shaft.

8. A method of performing a lithotripsy procedure, the method comprising:

contacting a stone comprising a physiological calculi with a shaft having a proximal end extending from a handpiece configured to be held by a user of a lithotripsy system, the shaft having a distal end configured to engage the physiological calculi;

applying energy from the shaft to the stone to fragment the stone, the energy generated by an energization source configured to generate the energy for breaking apart the physiological calculi;

applying a force to the stone from the distal end of the shaft via the handpiece to facilitate transfer of the energy to the stone; and providing an output of an amount of force that the shaft contacts the stone using a force indicating device connected to the handpiece, the force indicating device configured to provide feedback related to the force that is being applied to the physiological calculi by the distal end of the shaft by the user at the handpiece, the force indicating device comprising a slide moveable relative to the handpiece, an indicator post mounted to one of the slide and the handpiece, and indicia located on the other of the slide and the handpiece, wherein the indicator post is movable relative to the indicia to provide the feedback.

9. The method of claim 8, further comprising adjusting the applied force based on the output.

10. The method of claim 9, wherein the output comprises visual output.

11. The method of claim 10, further comprising determining if the applied force is within a desired range between a first visual indicator and a second visual indicator denoting excessive and inadequate force, respectively.

12. The method of claim 8, wherein the output comprises haptic feedback related to the applied force.

13. The method of claim 8, wherein the output comprises audio feedback related to the applied force.

14. The method of claim 8, wherein the output comprises indicia indicating different types of stones.

15. The method of claim 8, wherein the energy comprises ultrasonic energy, laser energy, ultrasound energy, pneumatic or hydraulic energy.

* * * * *